(12) United States Patent
Song

(10) Patent No.: US 7,897,360 B2
(45) Date of Patent: Mar. 1, 2011

(54) ENZYME DETECTION TECHNIQUES

(75) Inventor: Xuedong Song, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 265 days.

(21) Appl. No.: 11/640,458

(22) Filed: Dec. 15, 2006

(65) Prior Publication Data

US 2008/0145843 A1 Jun. 19, 2008

(51) Int. Cl.
*G01N 33/573* (2006.01)
(52) U.S. Cl. .................. 435/7.4; 435/4; 435/18; 435/23; 435/24; 435/287.7; 435/173.2; 436/514; 436/518
(58) Field of Classification Search .............. 435/4, 18, 435/23, 24, 287.7, 173.2, 7.4; 436/514, 518
See application file for complete search history.

(56) References Cited

U.S. PATENT DOCUMENTS

| | | | |
|---|---|---|---|
| 3,700,623 A | | 10/1972 | Keim |
| 3,772,076 A | | 11/1973 | Keim |
| 4,072,576 A | * | 2/1978 | Arwin et al. ............... 435/4 |
| 4,140,580 A | | 2/1979 | Gibson et al. |
| 4,275,149 A | | 6/1981 | Litman et al. |
| 4,537,657 A | | 8/1985 | Keim |
| 4,582,699 A | * | 4/1986 | Murray ..................... 435/7.4 |
| 4,614,723 A | | 9/1986 | Schmidt et al. |
| 4,637,979 A | | 1/1987 | Skjold et al. |
| 4,748,116 A | | 5/1988 | Simonsson et al. |
| 4,780,401 A | * | 10/1988 | Heusser et al. ............ 424/146.1 |
| 4,806,423 A | | 2/1989 | Hugl et al. |
| 4,812,369 A | * | 3/1989 | Hanai et al. .............. 428/425.9 |
| 4,814,271 A | | 3/1989 | Hugl et al. |
| 4,859,581 A | | 8/1989 | Nicolson et al. |
| 4,874,695 A | | 10/1989 | Pincus |
| 4,891,312 A | * | 1/1990 | Schaumann et al. .......... 435/7.4 |

(Continued)

FOREIGN PATENT DOCUMENTS

EP 0864864 A1 9/1998

(Continued)

OTHER PUBLICATIONS

Search Report and Written Opinion for PCT/IB2007/053960 dated Mar. 28, 2008.

(Continued)

*Primary Examiner* — Bao-Thuy L Nguyen
(74) *Attorney, Agent, or Firm* — Dority & Manning, P.A.

(57) ABSTRACT

A lateral flow assay device for detecting the presence or quantity of an enzyme or enzyme inhibitor is provided. The lateral flow assay device utilizes a molecular substrate to facilitate the detection of an enzyme or enzyme inhibitor via detection of the substrate and/or a product formed in an enzyme-catalyzed reaction of the substrate. In one embodiment, for example, upon contacting a molecular substrate, an enzyme catalyzes a reaction with the molecular substrate and forms a product. The lateral flow assay device also includes a detectable substance that may generate a detectable signal for determining the presence or amount of enzyme in a test sample. For example, the detectable substance may be directly or indirectly attached to a specific binding member that has affinity for the product. Following the enzyme catalyzed reaction, the product may bind the detectable substance which may, in turn, generate the detectable signal. The signal exhibited by the substance may then be used to indicate the presence or quantity of an enzyme or enzyme inhibitor within the test sample.

19 Claims, 7 Drawing Sheets

U.S. PATENT DOCUMENTS

| | | | |
|---|---|---|---|
| 5,059,522 A * | 10/1991 | Wayne | 435/7.2 |
| 5,075,077 A | 12/1991 | Durley, III et al. | |
| 5,124,254 A | 6/1992 | Hewlins et al. | |
| 5,252,459 A | 10/1993 | Tarcha et al. | |
| 5,292,652 A | 3/1994 | Dovey et al. | |
| 5,328,831 A | 7/1994 | Stewart et al. | |
| 5,449,612 A | 9/1995 | Lepargneur et al. | |
| 5,464,739 A | 11/1995 | Johnson et al. | |
| 5,464,741 A | 11/1995 | Hendrix | |
| 5,518,883 A | 5/1996 | Soini | |
| 5,571,684 A | 11/1996 | Lawrence et al. | |
| 5,573,909 A | 11/1996 | Singer et al. | |
| 5,585,273 A | 12/1996 | Lawrence et al. | |
| 5,585,279 A | 12/1996 | Davidson | |
| 5,591,581 A | 1/1997 | Massey et al. | |
| 5,637,509 A | 6/1997 | Hemmilä et al. | |
| 5,670,381 A | 9/1997 | Jou et al. | |
| 5,731,147 A | 3/1998 | Bard et al. | |
| 5,731,157 A * | 3/1998 | Miller et al. | 435/7.4 |
| 5,786,137 A | 7/1998 | Diamond et al. | |
| 5,922,537 A | 7/1999 | Ewart et al. | |
| 6,004,530 A | 12/1999 | Sagner et al. | |
| 6,022,698 A | 2/2000 | Chen et al. | |
| 6,030,840 A | 2/2000 | Mullinax et al. | |
| 6,197,537 B1 | 3/2001 | Rao et al. | |
| 6,235,464 B1 | 5/2001 | Henderson et al. | |
| 6,242,268 B1 | 6/2001 | Weider et al. | |
| 6,243,980 B1 | 6/2001 | Bronstein et al. | |
| 6,261,779 B1 | 7/2001 | Barbera-Guillem et al. | |
| 6,287,798 B1 | 9/2001 | James et al. | |
| 6,306,642 B1 | 10/2001 | Nelson | |
| 6,348,319 B1 | 2/2002 | Braach-Maksvytis et al. | |
| 6,362,011 B1 | 3/2002 | Massey et al. | |
| 6,402,918 B1 | 6/2002 | Schlenoff et al. | |
| 6,444,423 B1 | 9/2002 | Meade et al. | |
| 6,451,619 B1 | 9/2002 | Catt et al. | |
| 6,468,741 B1 | 10/2002 | Massey et al. | |
| 6,472,141 B2 | 10/2002 | Nikiforov | |
| 6,485,926 B2 | 11/2002 | Nemori et al. | |
| 6,528,321 B1 | 3/2003 | Fitzgerald et al. | |
| 6,582,930 B1 | 6/2003 | Ponomarev et al. | |
| 6,585,939 B1 | 7/2003 | Dapprich | |
| 6,613,583 B1 | 9/2003 | Richter et al. | |
| 6,623,955 B2 | 9/2003 | Matner et al. | |
| 6,670,198 B2 * | 12/2003 | Kimura | 436/518 |
| 7,041,469 B2 | 5/2006 | Lawrence et al. | |
| 7,094,528 B2 | 8/2006 | Song et al. | |
| 2001/0046668 A1 | 11/2001 | Levine et al. | |
| 2002/0127623 A1 | 9/2002 | Minshull et al. | |
| 2003/0073147 A1 | 4/2003 | Alderete et al. | |
| 2003/0108978 A1 | 6/2003 | Ciambrone et al. | |
| 2003/0119073 A1 | 6/2003 | Quirk et al. | |
| 2003/0119202 A1 | 6/2003 | Kaylor et al. | |
| 2003/0119204 A1 | 6/2003 | Wei et al. | |
| 2003/0124739 A1 | 7/2003 | Song et al. | |
| 2004/0002110 A1 | 1/2004 | Boga et al. | |
| 2004/0029205 A1 | 2/2004 | Small, Jr. et al. | |
| 2004/0043502 A1 | 3/2004 | Song et al. | |
| 2004/0043507 A1 | 3/2004 | Song et al. | |
| 2004/0043511 A1 | 3/2004 | Song et al. | |
| 2004/0043512 A1 | 3/2004 | Song et al. | |
| 2004/0081971 A1 | 4/2004 | Yue et al. | |
| 2004/0106190 A1 | 6/2004 | Yang et al. | |
| 2004/0121334 A1 | 6/2004 | Wei et al. | |
| 2004/0121480 A1 | 6/2004 | Wei | |
| 2005/0112703 A1 | 5/2005 | Song | |
| 2005/0112780 A1 | 5/2005 | Song | |
| 2005/0124072 A1 | 6/2005 | Boga | |
| 2005/0136529 A1 | 6/2005 | Yang et al. | |
| 2005/0136550 A1 | 6/2005 | Yang et al. | |
| 2005/0191704 A1 | 9/2005 | Boga et al. | |
| 2005/0220712 A1 | 10/2005 | Wright et al. | |
| 2005/0233368 A1 | 10/2005 | Beall et al. | |
| 2005/0243321 A1 | 11/2005 | Cohen et al. | |
| 2005/0244643 A1 | 11/2005 | Song et al. | |
| 2006/0003336 A1 | 1/2006 | Song et al. | |
| 2006/0003394 A1 | 1/2006 | Song et al. | |
| 2006/0019265 A1 | 1/2006 | Song et al. | |
| 2006/0057661 A1 | 3/2006 | Song et al. | |
| 2006/0127459 A1 | 6/2006 | Huang et al. | |
| 2007/0048182 A1 | 3/2007 | Song et al. | |
| 2007/0048807 A1 | 3/2007 | Song | |
| 2007/0048815 A1 | 3/2007 | Song | |
| 2007/0048816 A1 | 3/2007 | Song | |
| 2007/0134747 A1 | 6/2007 | DiGiammarino et al. | |

FOREIGN PATENT DOCUMENTS

| | | |
|---|---|---|
| WO | WO 9714028 | 4/1997 |
| WO | WO 2005066359 A1 | 7/2005 |
| WO | WO 2006079826 A1 | 8/2006 |
| WO | WO 2007096637 A1 | 8/2007 |
| WO | WO 2007128980 A1 | 11/2007 |

OTHER PUBLICATIONS

U.S. Appl. No. 11/399,687, filed Apr. 6, 2006, Enzymatic Detection Techniques, Song.

L.J. Jones et al.—Quenched BODIPY Dye-Labeled Casein Substrates for the Assay of Protease Activity by Direct Fluorescence Measurement—Published, *Analytical Biochemistry* 251, 144-152 (1997) Article No. AB972259.

J.M. Steiner et al.—Development and analytic validationof an enzyme-linked immunosorbent assay for the measurement of canine pancreatic lipase immunoreactivity in serum—Published, *The Canadian Journal of Veterinary Research* 2003; 67: 175-182.

H. Rahimi et al.—Monoclonal antibodies against *Candida rugosa* lipase—Published, *Journal of Molecular Catalysts B: Enzymatic* 28 (2004) 71-74.

D.A. Schofield et al.—Differential *Candida albicans* lipase gene expression during alimentary tract colonization and infection—Published, *FEMS Microbiology Letters* 244 (2005) 359-365.

F. Stehr et al.,—Expression analysis of the *Candida albicans* lipase gene family during experimental infections and in patient samples—Published, *FEMS Yeast Research* 4 (2004) 401-408.

Englert et al.—Layered Expression Scanning: Rapid Molecular Profiling of Tumor Samples—Published, *Cancer Research* 60, 1526:1530, Mar. 15, 2000.

A.W. Kusterbeck et al.—Use of the USDT flow immunosensor for quantitation of benzoylecgonine in urine—Published, *Elsevier Science Limited, Biosensors & Bioelectronics* vol. 11 No. 8 pp. 725-734, 1996.

D.J. Pritchard et al.—Simultaneous determination of follicle stimulating hormone and luteinising hormone using multianalyte immunosensor—Published, *Elsevier, Analytica Chimica Acta* 310 (1995) 251-256.

L.M. Golub et al.—A matrix metalloproteinase inhibitor reduces bone-type collagen degradation fragments and specific collagenases in gingival crevicular fluid during adult periodontitis—Published, *Inflamm. res.* 46 (1997) 310-319.

K. Brew et al.—Tissue inbibitors of metalloproteinases: evolution, structure and function—Published, *Elsevier—Biochimica et Biophysica Acta* 1477 (2000) 267-283.

B. Stratmann et al.—MMP-TIMP interaction depends on residue 2 in TIMP-4—Published, *FEBS Letters* 507 (2001) 285-287.

Osmanağaoğlu et al.—*Identification of Different Candida Species Isolated in Various Hospitals in Ankara by Fungichrom Test Kit and Their Differentiation by SED-Page*, Turk. J. Med. Sci., vol. 30, 2000, pp. 355-358.

Lorenz et al.—*Transcriptional Response of Candida albicans upon Internalization by Macrophages,* Eukaryotic Cell, vol. 3. No. 5, Oct. 2004, pp. 1076-1087.

Yuan et al.—*A New Tetradentate β-Diketonate-Europium Chelate That Can Be Covalently Bound to Proteins for Time-Resolved Fluoroimmunoassay,* Analytical Chemistry, vol. 70, No. 3, Feb. 1, 1998, pp. 596-601.

Lövgren et al—*One-step all-in-one dry reagent immunoassays with fluorescent europium chelate label and time-resolved fluorometry,*. Clinical Chemistry, vol. 42, No. 8, 1996, pp. 1196-1201.

* cited by examiner

ENZYME DETECTION TECHNIQUES

BACKGROUND

It is often desirable to determine the presence or quantity of a particular enzyme within a test sample. In some cases, the mere presence of an enzyme may, for example, indicate the existence of tissue or organ damage. Likewise, abnormal enzyme concentrations may also indicate other conditions, such as a bacterial or viral infection. For instance, proteases (e.g., aspartic proteases) and metallopeptidases are believed to increase the pathogenicity of *Candida albicans*, a microorganism that may cause candidal vaginitis ("yeast infection"). The presence or concentration of an enzyme in a test sample may also serve as a diagnostic marker for some types of cancers and other conditions. For instance, prostate-specific antigen (PSA) is a well-known marker for prostate cancer. Other examples of diagnostic markers include cathepsin B (cancer), cathepsin G (emphysema, rheumatoid arthritis, inflammation), plasminogen activator (thrombosis, chronic inflammation, cancer), and urokinase (cancer).

One conventional technique for detecting the presence of an enzyme is described in U.S. Pat. No. 6,348,319 to Braach-Maksvytis, et al. Braach-Maksvytis, et al. functions by sensing the digestion of a substrate by the enzyme. For example, FIG. 1 of Braach-Maksvytis, et al. illustrates a device 10 that includes a first zone 11 and a second zone 12. The first zone 11 is provided with polymer beads 13 (carrier) linked to streptavidin 14 (probe) via a peptide linker 15 that is cleavable by a protease 16. Upon addition of the protease 16, the streptavidin 14 is released and passes to the second zone 12, which includes a biosensor membrane 17 that detects the presence of streptavidin through a change in the impedance of the membrane. (Col. 5, ll. 25-30). Unfortunately, however, techniques such as described by Braach-Maksvytis, et al., are far too complex and cost prohibitive for certain types of applications, such as those requiring a relatively quick diagnosis by a patient (self-diagnosis or with the aid of medical personnel).

As such, a need currently exists for a simple and inexpensive technique to accurately detect the presence of an enzyme within a test sample.

SUMMARY

In accordance with one embodiment, a lateral flow assay device for detecting an enzyme, or an inhibitor thereof, within a test sample, is disclosed. The device comprises a chromatographic medium defining a detection zone, a molecular substrate, and a detectable substance capable of generating a detection signal. For example, the detection signal may be capable of being generated within the detection zone to determine the presence or quantity of an enzyme or an inhibitor thereof. In one embodiment, a receptive material may be immobilized within the detection zone that is capable of binding to the enzyme reaction product or complexes thereof. In one embodiment, a chromatographic medium may further define a second detection zone within which a second detection signal is capable of being generated. For example, a second receptive material may be immobilized within the second detection zone that is capable of binding to the molecular substrate or complexes thereof.

In accordance with another embodiment, a method for detecting an enzyme, or an inhibitor thereof, within a test sample, is disclosed. The method comprises providing a lateral flow testing device comprising a chromatographic medium that defines a detection zone. The lateral flow device includes a molecular substrate that is capable of undergoing a catalyzed reaction to form a product and a detectable substance for directly or indirectly generating a detection signal. The method includes contacting the chromatographic medium with a test sample and determining the presence or intensity of a detection signal in the detection zone. In some embodiments, the chromatographic medium can define additional zones. For example, the chromatographic medium may define an application area within which the test sample may contact the molecular substrate. In one embodiment, the chromatographic medium may define a conjugate zone downstream of an application area and within which a detectable substance may be diffusibly immobilized. Competitive or sandwich immunoassays may be employed to determine the presence or concentration of the enzyme within the test sample.

Other features and aspects of the present disclosure are discussed in greater detail below.

BRIEF DESCRIPTION OF THE DRAWINGS

A full and enabling disclosure of the subject matter, including the best mode thereof, directed to one of ordinary skill in the art, is set forth more particularly in the remainder of the specification, which makes reference to the appended figures in which.

Figure 1:
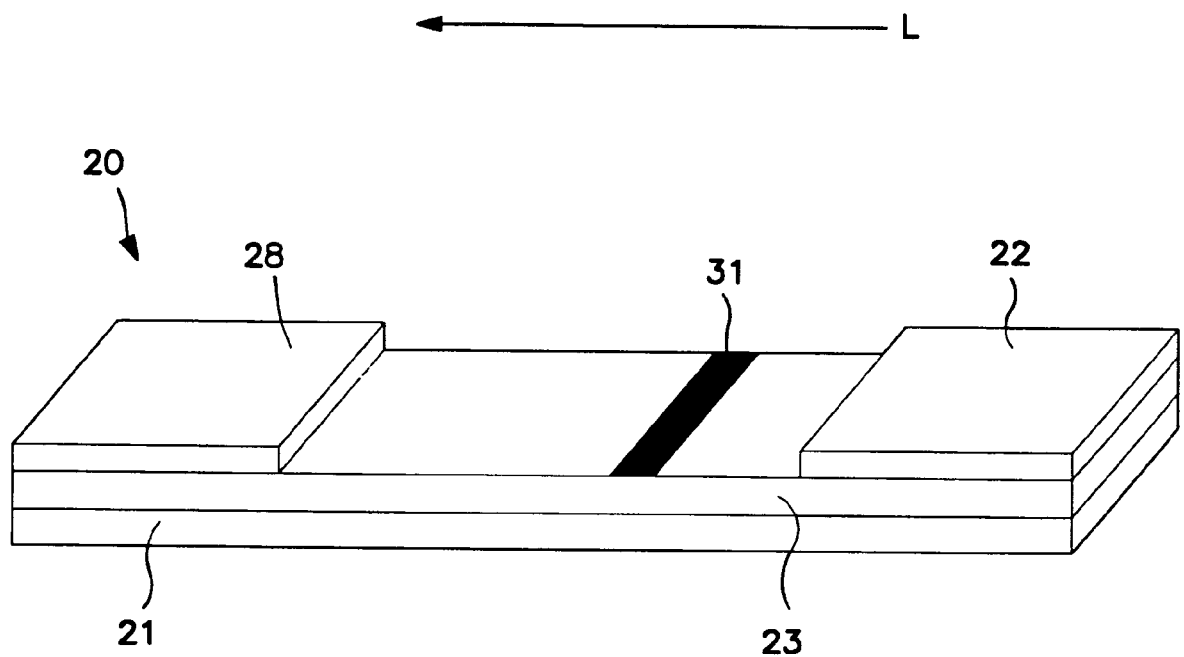
FIG. 1 is a perspective view of one embodiment of an assay device that may be used in a lateral flow assay device.

Repeat use of reference characters in the present specification and drawings is intended to represent same or analogous features or elements.

DETAILED DESCRIPTION OF REPRESENTATIVE EMBODIMENTS

Definitions

As used herein, the term "test sample" generally refers to a material suspected of containing an enzyme and/or enzyme inhibitor. For example, the test sample may be obtained or derived from a biological source, such as a physiological fluid, including, blood, interstitial fluid, saliva, ocular lens fluid, cerebral spinal fluid, sweat, urine, milk, ascites fluid, mucous, synovial fluid, peritoneal fluid, vaginal fluid, amniotic fluid, and so forth. Besides physiological fluids, other liquid samples may be used such as water, food products, and so forth, for the performance of environmental or food production assays. In addition, a solid material may be used as the test sample. The test sample may be used directly as obtained from a source or following a pretreatment to modify the character of the sample. For example, such pretreatment may include preparing plasma from blood, diluting viscous fluids, and so forth. Methods of pretreatment may also involve filtration, precipitation, dilution, distillation, mixing, concentration, inactivation of interfering components, the addition of reagents, etc. Moreover, it may also be beneficial to modify a solid test sample to form a liquid medium, to release the enzyme and/or enzyme inhibitor, etc.

As used herein, the term "molecular substrate" generally refers to a molecular compound that may undergo an enzyme-catalyzed reaction to form a product. In one embodiment, a molecule substrate may be less than about 3000 Daltons (i.e., atomic mass units, one Dalton being equivalent to $\frac{1}{12}$ of the atomic mass of the most abundant carbon isotope $^{12}C$). In certain embodiments, a molecule substrate may be smaller, for instance less than about 2000 Daltons, less than about 1000 Daltons, or less than about 500 Daltons. In one embodiment, a molecular substrate may be free of (i.e., not bound or otherwise attached to) secondary compounds, structures or materials that may interfere sterically, chemically, or in any other fashion with interaction between a molecular substrate and an enzyme. For instance, a molecular substrate may be, in one embodiment, free of any reporter, bead, particle, tag, or the like.

As used herein, the term "substrate conjugate" generally refers to a molecular substrate that is bound or otherwise attached to a secondary material such as a probe, a particle, a bead, or the like.

DETAILED DESCRIPTION

Reference now will be made in detail to various embodiments of the disclosed subject matter, one or more examples of which are set forth below. Each example is provided by way of explanation, not limitation. In fact, it will be apparent to those skilled in the art that various modifications and variations may be made in the present disclosure without departing from the scope or spirit of the subject matter. For instance, features illustrated or described as part of one embodiment, may be used on another embodiment to yield a still further embodiment. Thus, it is intended that the present disclosure covers such modifications and variations as come within the scope of the appended claims and their equivalents.

The present disclosure is generally directed to a lateral flow assay device for detecting the presence or quantity of an enzyme or enzyme inhibitor. The assay device utilizes a molecular substrate such as, for example, a peptide, protein, or glycoprotein substrate, to facilitate the detection of the enzyme or enzyme inhibitor. The molecular substrate provides a target for an enzyme, such as a proteolytic enzyme. Specifically, upon contacting the molecular substrate, a proteolytic enzyme cleaves the molecular substrate and releases an enzyme reaction product. The assay device also utilizes a detectable substance that may generate a detection signal upon reaction of an enzyme with the molecular substrate. The signal generated by the detectable substance may then be used to indicate the presence or quantity of an enzyme or enzyme inhibitor within a test sample.

Various types of enzymes may be detected in accordance with the present disclosure. For instance, transferases, hydrolases, lyases, and so forth, may be detected. In some embodiments, the enzyme of interest is a "hydrolase" or "hydrolytic enzyme", which refers to enzymes that catalyze hydrolytic reactions. Examples of such hydrolytic enzymes include, but are not limited to, proteases, peptidases, lipases, nucleases, homo- or hetero-oligosaccharidases, homo- or hetero-polysaccharidases, phosphatases, sulfatases, neuraminidases and esterases. In one embodiment, for example, peptidases may be detected. "Peptidases" are hydrolytic enzymes that cleave peptide bonds found in shorter peptides. Examples of peptidases include, but are not limited to, metallopeptidases; dipeptidylpeptidase I, II, or IV; and so forth. In another embodiment, proteases may be detected. "Proteases" are hydrolytic enzymes that cleave peptide bonds found in longer peptides and proteins. Examples of proteases that may be detected include, but are not limited to, serine proteases (e.g., chymotrypsin, trypsin, elastase, PSA, etc.), aspartic proteases (e.g., pepsin), thiol proteases (e.g., prohormone thiol proteases), metalloproteases, acid proteases, and alkaline proteases. Still other enzymes are described in U.S. Pat. No. 6,243,980 to Bronstein, et al. and 2004/0081971 to Yue, et al., which are incorporated herein in their entirety by reference thereto for all purposes.

In addition to enzymes that cleave a molecular substrate, such as those described above, the assay device may alternatively be utilized to detect the presence of an enzyme that catalyzes the formation of a bond on a molecular substrate as well as enzymes that catalyze a conformational change in a molecular substrate. For instance, transferases, which transfer a functional group to a substrate, ligases, which covalently bond a second molecule to a substrate, polymerases, or isomerases may be detected. Exemplary transferases that may be detected include kinases and methylases. For instance, kinases including protein kinases, creatine kinases, hexokinase, and so forth may be detected through detection of the phosphorylation of the substrate. Methylases such as methylase II may be detected through the addition of one or more methyl groups to the substrate.

Likewise, any of a variety of known enzyme inhibitors may also be detected in accordance with the present disclosure. For example, known inhibitors of hydrolytic enzymes include, but are not limited to, inhibitors of proteases, peptidases, lipases, nucleases, homo- or hetero-oligosaccharidases, homo- or hetero-polysaccharidases, phosphatases, sulfatases, neuraminidases and esterases. Protease inhibitors may include, for instance, aspartic protease inhibitors, serine protease inhibitors, thiol protease inhibitors, metalloprotease inhibitors, acid or alkaline protease inhibitors, and so forth. Some specific examples of protease inhibitors include benzamideine, indole, pepstatin, ovomacroglobulin, haloperidol, transition state mimetics, and so forth. Some specific examples of transferase inhibitors include ethacrynic acid, which inhibits glutathione S-transferase and sarasar®, a benzocycloheptapyridyl Farnesyl Transferase Inhibitor (FTI).

As stated above, molecular substrates may be used to detect the presence or quantity of an enzyme or enzyme inhibitor. The molecular substrate may occur naturally or be synthetic. Some suitable molecular substrates for hydrolytic enzymes include, for instance, esters, amides, peptides, ethers, or other chemical compounds having an enzymatically-hydrolyzable bond. The enzyme-catalyzed hydrolysis reaction may, for example, result in a hydroxyl or amine compound as one product, and a free phosphate, acetate, etc., as a second product. Specific types of molecular substrates may include, for instance, proteins or glycoproteins, peptides, nucleic acids (e.g., DNA and RNA), carbohydrates, lipids, esters, derivatives thereof, and so forth. For instance, some suitable molecular substrates for peptidases and/or proteases may include peptides, proteins, and/or glycoproteins, such as casein (e.g., β-casein, azocasein, etc.), albumin (e.g., bovine serum albumin (BSA)), hemoglobin, myoglobin, keratin, gelatin, insulin, proteoglycan, fibronectin, laminin, collagen, elastin, and so forth. Still other suitable molecular substrates are described in U.S. Pat. No. 4,748,116 to Simonsson, et al.; U.S. Pat. No. 5,786,137 to Diamond, et al.; U.S. Pat. No. 6,197,537 to Rao, et al.; and U.S. Pat. No. 6,235,464 to Henderson, et al.; U.S. Pat. No. 6,485,926 to Nemori, et al., which are incorporated herein in their entirety by reference thereto for all purposes.

Following contact of a molecular substrate with an enzyme, an enzyme reaction product may form. The molecule substrate or the enzyme reaction product may interact with a detectable substance so as to directly or indirectly generate a detectable signal. Suitable detectable substances may include, for instance, chromogens; luminescent compounds (e.g., fluorescent, phosphorescent, etc.); radioactive compounds; visual compounds (e.g., latex or metallic particles, such as gold); liposomes or other vesicles containing signal-producing substances; enzymes and/or substrates, and so forth. For instance, some enzymes suitable for use as detectable substances are described in U.S. Pat. No. 4,275, 149 to Litman, et al., which is incorporated herein in its entirety by reference thereto for all purposes. One example of an enzyme/substrate system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. Other suitable detectable substances may be those described in U.S. Pat. No. 5,670,381 to Jou, et al. and U.S. Pat. No. 5,252,459 to Tarcha, et al., which are incorporated herein in their entirety by reference thereto for all purposes.

In some embodiments, the detectable substance may contain a luminescent compound that produces an optically detectable signal. The luminescent compound may be a molecule, polymer, dendrimer, particle, and so forth. For example, suitable fluorescent molecules may include, but are not limited to, fluorescein, europium chelates, phycobiliprotein, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or nonaqueous environment. For example, some suitable examples of ligands include, but are not limited to, pyridine; pyrazine; isonicotinamide; imidazole; bipyridine; terpyridine; phenanthroline; dipyridophenazine; porphyrin, porphine, and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc (II)-coproporphyrin-I, derivatives thereof, and so forth. Similarly, some suitable porphine complexes that are capable of exhibiting phosphorescent properties include, but not limited to, platinum (II) tetra-meso-fluorophenylporphine and palladium(II) tetra meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart, et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are not limited to, bis[(4,4'-carbomethoxy)-2,2'-bipyridine] 2-[3-(4-methyl-2,2'-bipyridine-4-yl)propyl]-1,3-dioxolane ruthenium (II); bis(2, 2'bipyridine)[4-(butan-1-al)-4'-methyl-2,2'-bi-pyridine] ruthenium (II); bis(2,2'-bipyridine)[4-(4'-methyl-2,2'-bipyridine-4'-yl)-butyric acid] ruthenium (II); tris(2, 2'bipyridine)ruthenium (II); (2,2'-bipyridine) [bis-bis(1,2-diphenylphosphino)ethylene] 2-[3-(4-methyl-2,2'-bipyridine-4'-yl)propyl]-1,3-dioxolane osmium (II); bis(2,2'-bipyridine)[4-(4'-methyl-2,2'-bipyridine)-butylamine] ruthenium (II); bis(2,2'-bipyridine)[1-bromo-4(4'-methyl-2, 2'-bipyridine-4-yl)butane]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein in their entirety by reference thereto for all purposes.

In some cases, "time-resolved" luminescent detection techniques are utilized. Time-resolved detection involves exciting a luminescent compound with one or more short pulses of light, then typically waiting a certain time (e.g., between approximately 1 to 100 microseconds) after excitation before measuring the remaining luminescent signal. In this manner, any short-lived phosphorescent or fluorescent background signals and scattered excitation radiation are eliminated. This ability to eliminate much of the background signals may result in sensitivities that are 2 to 4 orders greater than conventional fluorescence or phosphorescence. Thus, time-resolved detection is designed to reduce background signals from the emission source or from scattering processes (resulting from scattering of the excitation radiation) by taking advantage of the characteristics of certain luminescent materials.

To function effectively, time-resolved techniques generally require a relatively long emission lifetime for the luminescent compound. This is desired so that the compound emits its signal well after any short-lived background signals dissipate. Furthermore, a long luminescence lifetime makes it possible to use low-cost circuitry for time-gated measurements. For example, the detectable compounds may have a luminescence lifetime of greater than about 1 microsecond, in some embodiments greater than about 10 microseconds, in some embodiments greater than about 50 microseconds, and in some embodiments, from about 100 microseconds to about 1000 microseconds. In addition, the compound may also have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, one suitable type of fluorescent compound for use in time-resolved detection techniques includes lanthanide chelates of samarium (Sm (III)), dysprosium (Dy (III)), europium (Eu (III)), and terbium (Tb (III)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have exceptionally large Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent compound. In addition, these chelates have a narrow emission spectra, typically having bandwidths less than about 10 nanometers at about 50% emission. One suitable europium chelate is N-(p-isothiocyanatobenzyl)-diethylene triamine tetraacetic acid-$Eu^{+3}$.

In addition, lanthanide chelates that are inert, stable, and intrinsically fluorescent in aqueous solutions or suspensions may also be used to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino]methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate β-diketonate-europium chelate [Ref: Yuan, J. and Matsumoto, K.; Anal. Chem. 70, 596-601 (1998)]. In addition to the fluorescent compounds described above, other compounds that are suitable for use may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein in their entirety by reference thereto for all purposes.

As stated, a molecular substrate or a product of an enzyme catalyzed reaction may interact with a detectable substance to generate a detectable signal. For instance, an enzyme reaction product may specifically bind with a compound which in turn may bind to a detectable substance. For example, in some embodiments, an enzyme reaction product may be a member of a specific binding pair, i.e., two different molecules where one of the molecules chemically and/or physically binds to the second molecule. Immunoreactive specific binding members may include antigens, haptens, antibodies (primary or secondary), and complexes thereof, including those formed by recombinant DNA methods or peptide synthesis. An antibody may be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art. Other common specific binding members include, but are not limited to, biotin and avidin, streptavidin, neutravidin, captavidin, or an anti-biotin antibody; protein A and G; carbohydrates and lectins, complementary nucleotide sequences (including probe and capture nucleic acid sequences used in DNA hybridization assays to detect a target nucleic acid sequence); complementary peptide sequences including those formed by recombinant methods; effector and receptor molecules; hormone and hormone binding protein; enzyme cofactors and enzymes, enzyme inhibitors and enzymes; derivatives thereof, and so forth. Furthermore, specific binding pairs may include members that are analogs, derivatives, and/or fragments of the original specific binding member. When used to indirectly generate a signal, an enzyme reaction product that is a member of a specific binding pair may be placed into contact with a detectable substance conjugated with another member of the specific binding pair. Thus, the enzyme reaction product will indirectly bind to the detectable substance via the specific binding pair. The signal may then be readily detected (directly or indirectly) using techniques well known to those skilled in the art.

Regardless of whether an enzyme reaction product or an unreacted molecular substrate directly or indirectly binds a detectable substance, a detectable substance may be bound to or contain particles (sometimes referred to as "beads" or "microbeads"). Among other things, particles enhance the ability of the detectable substance to travel through a chromatographic medium and become immobilized within a detection zone, as further described below. For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex particles are labeled with a fluorescent or colored dye. Although any latex particle may be used, the latex particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al. and U.S. Pat. No. 5,252,459 to Tarcha, et al. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. of Eugene, Oreg. In addition, commercially available examples of suitable colored, latex microparticles include carboxylated latex beads sold by Bangs Laboratories, Inc. of Fishers, Ind.

When utilized, the shape of the particles may generally vary. In one particular embodiment, for instance, the particles are spherical in shape. However, it should be understood that other shapes are also contemplated by the present disclosure, such as plates, rods, discs, bars, tubes, irregular shapes, etc. In addition, the size of the particles may also vary. For instance, the average size (e.g., diameter) of the particles may range from about 0.1 nanometers to about 1,000 microns, in some embodiments, from about 0.1 nanometers to about 100 microns, and in some embodiments, from about 1 nanometer to about 10 microns. For instance, "micron-scale" particles are often desired. When utilized, such "micron-scale" particles may have an average size of from about 1 micron to about 1,000 microns, in some embodiments from about 1 micron to about 100 microns, and in some embodiments, from about 1 micron to about 10 microns. Likewise, "nano-scale" particles may also be utilized. Such "nano-scale" particles may have an average size of from about 0.1 to about 10 nanometers, in some embodiments from about 0.1 to about 5 nanometers, and in some embodiments, from about 1 to about 5 nanometers.

During use, a user may allow the test sample to contact the molecular substrate for a certain period of time. For example, those skilled in the art readily recognize that the time of contact between the reactants to ensure an enzyme-catalyzed reaction depends on the activity of the enzyme of interest, which in turn depends on in part on the temperature, pH, substrate concentration, the presence of inhibitors (competitive (binds to enzyme), uncompetitive (binds to enzyme-substrate complex), or noncompetitive (binds to enzyme and/or enzyme-substrate complex)), and so forth. These factors may be selectively controlled as desired to increase or decrease the contact time. For example, the contact time may be greater than about 1 minute, in some embodiments from about 5 to about 50 minutes, and in some embodiments, from about 10 to about 25 minutes. Likewise, the pH may be selectively controlled to facilitate enzyme activity. For example, high levels of basic substances (e.g., amines) within a test sample may result in a pH that is too high for optimum activity of some enzymes, e.g., greater than 8. Specifically, an enzyme may possess optimum activity at a pH level of from about 3 to about 8, and in some embodiments, from about 4 to about 7. Thus, if desired, a buffer or other pH-altering compound may be employed to maintain the desired pH. Similarly, the temperature may be selectively controlled using a heating or cooling system to facilitate the enzyme activity.

Following contact, any enzyme present within the test sample will typically interact with at least a portion of the substrate molecules. As a result, various species may be formed, including enzyme reaction products, partially cleaved complexes (e.g., enzyme-substrate complexes), unreacted substrate molecules, and secondary reactants and products of the enzyme-catalyzed reaction. For instance, in the case of a hydrolytic enzyme, at least two products (which may be the same or different) formed during the enzyme-catalyzed cleavage of the substrate molecule will be included in the mixture. When considering an enzyme-catalyzed reaction in which new bonds are formed on the substrate, materials included in the mixture may include other reactants involved in the reaction (e.g., ATP, methyl-donating reactants, monomers such as amino acids, and nucleotides that may be added to the substrate by a polymerase or a ligase, etc.) as well as secondary products formed in the enzyme-catalyzed reaction (e.g., ADP).

Longer contact times and greater enzyme concentrations may result in a greater concentration of enzyme reaction products in the resulting mixture, for instance in the case of a multiple stage enzyme reaction, a longer contact time may allow the multiple reactions to proceed farther to completion. Accordingly, some embodiments include a method for selectively controlling the contact time of the components of the process. For instance, following contact with the molecular substrate, the test sample may be contained in an area of a device according to any flow control means (e.g., flow restriction via physical design of a device, material selection of a device, and the like) so as to selectively control the contact time of the various components.

During and/or following a time of contact with the molecular substrate, the test sample may contact a detectable substance that may generate a detectable signal. For example, a detectable substance may directly or indirectly bind an enzyme reaction product as it is formed. Generally speaking, as enzyme concentration begins to increase in the test sample, more enzyme reaction product will form in the mixture. Consequently, enzyme concentration correlates to the quantity of the enzyme reaction product of the mixture. If the enzyme reaction product is capable of directly binding a detectable substance to generate a detection signal (e.g., luminescent compounds, colored dyes, etc.), the presence or intensity of the detection signal may be determined qualitatively, quantitatively, or semi-quantitatively with relative ease. For example, in one embodiment, the amount of enzyme is directly proportional to the signal intensity of the enzyme product bound to the detectable substance. If desired, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

In some cases, it may be preferred to bring the test sample into contact with a detectable substance following a period of time during which the test sample interacts with the molecular substrate and any other desired reagents, e.g., buffers, etc. For example, it may be desired to utilize components other than an enzyme reaction product to determine the presence or intensity of a detection signal. In one embodiment, a detectable substance may directly or indirectly bind the molecular substrate of a mixture. Accordingly, the test sample may be brought into contact with the detectable substance following a period of contact during which an enzyme in the test sample may react with the molecular substrate. In this embodiment, the amount of enzyme may be indirectly proportional to the signal intensity of the substrate bound to the detectable substance.

In any case, disclosed detection methods may provide a dual amplification enzyme detection method. In particular, a method may include a first enzyme reaction amplification followed by a second signal amplification. The two-stage amplification method may enhance the sensitivity and/or accuracy of detection. Moreover, the disclosed methods may provide enzyme reaction amplification with an effective reaction time and sample volume control scheme. In addition, the disclosed methods may differentiate between active and non-active forms of an enzyme in a convenient assay method without the need for a deactivating step as is required in many previously known enzymatic assays.

In this regard, various embodiments of an assay device that may optionally be used to facilitate detection will now be described in more detail. Referring to FIG. 1, for instance, one embodiment of an assay device 20 is shown that contains a chromatographic medium 23 carried by a support 21. The chromatographic medium 23 may be made from any of a variety of materials through which a fluid is capable of passing, such as a fluidic channel, porous membrane, etc. For example, the chromatographic medium 23 may be a porous membrane formed from materials such as, but not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the chromatographic medium is formed from nitrocellulose and/or polyether sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms. Although not required, the use of the chromatographic medium 23 for chemical separation may provide enhanced benefits over other conventional separation techniques, such as centrifugation. For example, the chromatographic medium 23 may simplify and reduce the costs of the resulting lateral flow assay device for many consumer applications, including those in which a disposable kit is desired.

The support 21 may be formed from any material able to carry the chromatographic medium 23. Although not required, the support 21 may be transparent so that light readily passes therethrough. In addition, it is also generally desired that the support 21 is liquid-impermeable so that fluid flowing through the medium does not leak through the support 21. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. As is well known the art, the chromatographic medium 23 may be cast onto the support 21, wherein the resulting laminate may be die-cut to the desired size and shape. Alternatively, the chromatographic medium 23 may simply be laminated to the support 21 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate structures are described in U.S. Pat. No. 5,075,077 to Durley, III, et al., which is incorporated herein in its entirety by reference thereto for all purposes.

The assay device 20 may also utilize an absorbent material 28. The absorbent material 28 generally receives fluid that has migrated through the entire chromatographic medium 23. As is well known in the art, the absorbent material 28 may assist in promoting capillary action and fluid flow through the medium 23.

In the embodiment illustrated in FIG. 1, the test sample may be applied directly to conjugate pad 22. Provided reagents may include one or more molecular substrates, co-factors, buffers, inhibitors, or other reagents useful to promote the enzyme reaction. For instance, for assaying a test sample that beneficially requires a diluent, provided reagents may include a predetermined amount of diluent in addition to other reagents. The test sample may be added to the diluent to initiate an enzyme reaction. The provided reagents may be provided together or separately, as desired. For example, a diluent may be physically separated from other reagents. Following addition of a test sample to a diluent, for instance in a mixing well formed on the device, the mixture may be contacted with additional reagents. In the illustrated embodiment, contact is carried out during and following combination of the test sample with the reagents provided at the conjugate pad.

The conjugate pad 22 is in fluid communication with the porous membrane 23 through which the mixture may travel in the direction illustrated by arrow "L" in FIG. 1. Some suitable materials that may be used to form the conjugate pad 22 include, but are not limited to, nitrocellulose, cellulose, porous polyethylene pads, and glass fiber filter paper. The conjugate pad 22 may include a detectable substance diffusibly immobilized thereto to which a component of the mixture may preferentially bind (either directly or non-directly). For example, the conjugate pad 22 may include a diffusibly immobilized probe labeled with a detectable substance, the probe additionally including a specific binder for an enzyme reaction product, the molecular substrate, or another component of the mixture. Accordingly, a conjugated probe including a detectable substance and a component of the mixture may be formed. The component of the mixture, e.g., an enzyme reaction product, may be conjugated to the probes using any of a variety of well-known techniques, such as through covalent bonding and/or physical adsorption in a manner such as described above. In one particular embodiment, carboxylic groups of the probe are activated and reacted with amino groups of an enzyme reaction product to form an amide bond. If desired, the conjugate pad 22 may also contain one or more assay reagents either diffusibly or non-diffusibly immobilized thereto, e.g., buffers, inhibitors, and the like.

Regardless, the chromatographic medium 23 defines a detection zone 31 within which the conjugated probe may be captured and detected. The manner in which the conjugated probe is captured may depend on the nature of the probe. For example, in some embodiments, a biological receptive material may be immobilized within the detection zone 31 for capturing biological components. Such biological receptive materials are well known in the art and may include, but are not limited to, antibodies, antigens, haptens, biotin, avidin, streptavidin, neutravidin, captavidin, protein A, protein G, carbohydrates, lectins, nucleotide sequences, peptide sequences, effector and receptor molecules, hormone and hormone binding protein, enzyme cofactors and enzymes, enzyme inhibitors and enzymes, and derivatives thereof.

Of course, any other suitable technique for capturing and detecting the conjugated probes may also be used. For example, in some embodiments, non-biological receptive materials may be immobilized within the detection zone 31 for capturing probes. For instance, in one embodiment, the receptive material is a polyelectrolyte. Polyelectrolytes may have a net positive or negative charge, as well as a net charge that is generally neutral. Some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyldimethyl-ammonium chloride; cationic cellulose derivatives, such as cellulose copolymers or cellulose derivatives grafted with a quaternary ammonium water-soluble monomer; and so forth. In one particular embodiment, CelQuat® SC-230M or H-100 (available from National Starch & Chemical, Inc.), which are cellulosic derivatives containing a quaternary ammonium water-soluble monomer, may be utilized. Moreover, some suitable examples of polyelectrolytes having a net negative charge include, but are not limited to, polyacrylic acids, such as poly(ethylene-co-methacrylic acid, sodium salt), and so forth. It should also be understood that other polyelectrolytes may also be utilized in the disclosed methods, such as amphiphilic polyelectrolytes (i.e., having polar and non-polar portions). For instance, some examples of suitable amphiphilic polyelectrolytes include, but are not limited to, poly(styryl-b-N-methyl 2-vinyl pyridinium iodide) and poly(styryl-b-acrylic acid), both of which are available from Polymer Source, Inc. of Dorval, Canada. Further examples of polyelectrolytes are described in more detail in U.S. Patent App. Publication No. 2003/0124739 to Song, et al., which is incorporated herein in it entirety by reference thereto for all purposes.

Although any polyelectrolyte may generally be utilized, the polyelectrolyte selected for a particular application may vary depending on the nature of the conjugated probes. In particular, the distributed charge of a polyelectrolyte allows it to bind to substances having an opposite charge. Thus, for example, polyelectrolytes having a net positive charge are often better equipped to bind with conjugated probes (e.g., dyed particles) that are negatively charged, while polyelectrolytes that have a net negative charge are often better equipped to bind to conjugated probes that are positively charged. Thus, in such instances, the ionic interaction between these molecules allows the required binding to occur within the detection zone 31. Nevertheless, although ionic interaction is primarily utilized to achieve the desired binding, it has also been discovered that polyelectrolytes may bind with probes having a similar charge.

According to one embodiment, an enzyme reaction product conjugated to the probe including the detectable substance may have an affinity for the receptive material within the detection zone 31. In this instance, the conjugated probe may become immobilized within the detection zone 31 through specific binding between the enzyme reaction product and a receptive material so that the signal generated by the detectable substance may be detected. For example, the enzyme reaction product may be bound to the probe via a first specific binding site and the enzyme reaction product may contain a second specific binding site that exhibits a specific affinity for the receptive material.

The detection zone 31 may generally provide any number of distinct detection regions so that a user may better determine the concentration of an enzyme within a test sample. When utilized, each region may contain the same or different receptive materials. For example, the detection zone 31 may include two or more distinct detection regions (e.g., lines, dots, etc.). The use of two or more distinct detection regions may provide certain benefits, such as facilitating semi-quantitation and/or inhibiting potential false positives due to overrunning of the reactive complexes or other materials. The detection regions may be disposed in the form of lines in a direction substantially perpendicular to the flow of the test sample through the chromatographic medium 23. Likewise, in some embodiments, the detection regions may be disposed in the form of lines in a direction substantially parallel to the flow of the test sample through the medium 23.

For the embodiment shown in FIG. 1, as enzyme concentration increases in a test sample, more conjugated probes are formed and become immobilized within the detection zone 31. The increased quantity of detectable enzyme reaction products at the detection zone 31 results in an increase in signal intensity. From this increase in signal intensity, the presence or concentration of the enzyme may be readily determined. For example, in one embodiment, the amount of enzyme is directly proportional to the signal intensity at the detection zone 31, $I_1$. If desired, the signal intensity $I_1$ may be plotted versus the enzyme concentration for a range of known enzyme concentrations to generate an intensity curve. To determine the quantity of enzyme in an unknown test sample, the signal intensity may then be converted to enzyme concentration according to the intensity curve.

It should be understood that one or more distinct regions of the detection zone 31 may exhibit the above-described relationship between signal intensity and enzyme concentration; however, each distinct region need not exhibit such a relationship. For example, in some embodiments, only one of multiple distinct regions may exhibit a signal intensity that is directly proportional to the concentration of the enzyme. The signal intensity of other distinct regions, such as those used to reduce false positives, may otherwise remain constant, or exhibit an increase and/or decrease in signal intensity. So long as at least one distinct region of the detection zone 31 satisfies the direct relationship, the signal intensity exhibited by the detection zone 31 is considered directly proportional to the enzyme concentration.

Figure 2:
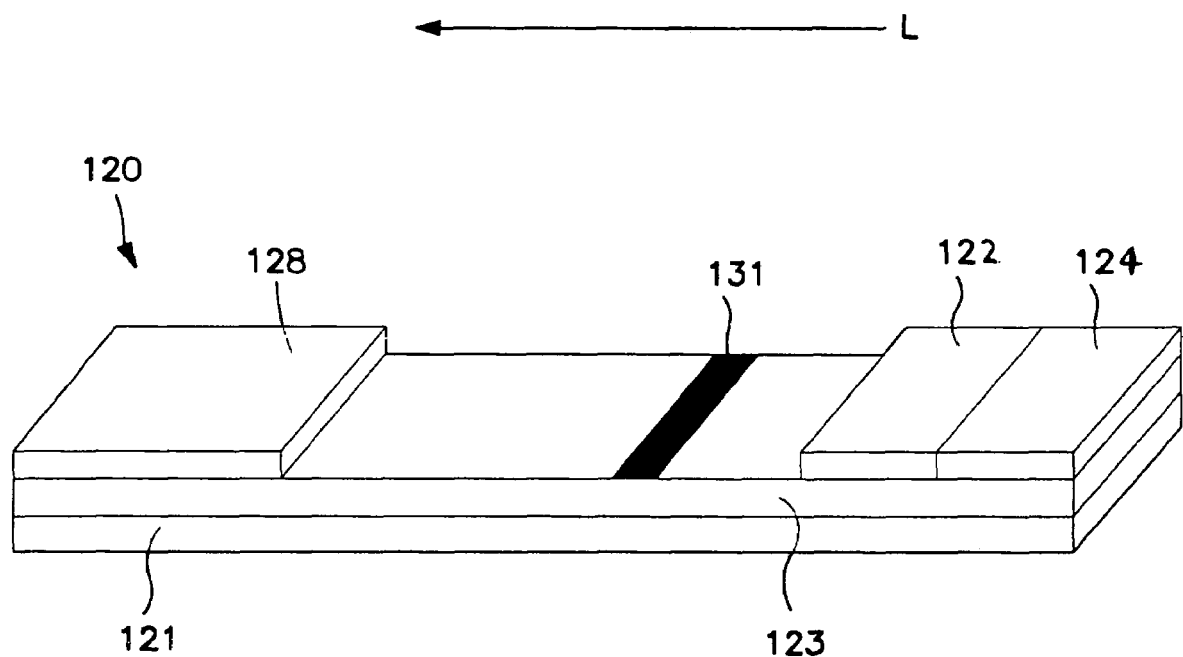
FIG. 2 is a perspective view of another embodiment of an assay device that may be used in a lateral flow assay device.

Certain embodiments of the disclosed subject matter may utilize a sample application area on the assay device. Thus, a test sample may be directly applied to a device upstream of the conjugate pad 22. In this regard, various embodiments of applying a test sample to a device including a sample application area will now be described in more detail. Referring to FIG. 2, for example, an assay device 120 is shown that includes a chromatographic medium 123 positioned on a support 121, an absorbent material 128, and a sample application pad 124. A test sample is directly applied to the sample application pad 124. The sample application pad 124 may contain one or more assay pretreatment reagents, either diffusibly or non-diffusibly immobilized thereto. For instance, the sample application pad 124 may contain one or more molecular substrates, co-factors, buffers, inhibitors, or other reagents useful to promote the enzyme reaction. The substrate and enzyme may contact one another and be allowed to interact within the mixture formed upon the application of the test sample to the sample application pad 124. Thus, the sample application pad 124 may in effect define a reaction zone on the device. In some embodiments, the contact time/reaction time may be more specifically controlled through utilization of a sample application pad 124. For example, porosity of the sample application pad 124 may be controlled to control flow rate of the mixture from the sample application pad 124 to the adjacent sections of the device 120. In another embodiment, the sample application pad 124 may be temporarily separated from adjacent areas of the device 120 through barriers. For instance, the sample application pad may define a well within which the mixture may be formed and held. Following the desired contact period, a temporary barrier, e.g., a gate, may be removed and the mixture may flow via a porous membrane, a fluidic channel, or the like, to a conjugate pad 122.

Probes capable of generating a detectable signal may be diffusibly immobilized to the conjugate pad 122 that are configured to bind to a component of the mixture. For example, the probes may contain a detectable substance, such as described above. The probes may also contain particles labeled or otherwise applied with the detectable substance. In some instances, it is desired to modify the probes in some manner. For example, the probes may be modified with a specific binding member to form probes that have specific affinity for an enzyme reaction product, a molecular substrate, or another component of the mixture. The specific binding members may generally be applied to the probes using any of a variety of well-known techniques, such as through covalent bonding and/or physical adsorption in a manner such as described above. In one particular embodiment, carboxylic groups on the probe surface are activated and reacted with amino groups of the specific binding member to form an amide bond.

Regardless of its particular configuration, the assay device 120 typically includes a detection zone 131 within which a component of the mixture, e.g., an enzyme reaction product, may be captured and detected. The enzyme reaction product may be detected within the detection zone 131 utilizing a variety of assay formats. In one embodiment, for example, a "sandwich" assay format is utilized in which the specific binding member of a probe is selected to have an affinity for the enzyme reaction product. The enzyme reaction product, such as antibodies, antigens, etc., typically has two or more binding sites (e.g., epitopes). One of these binding sites becomes occupied by the specific binding member of the probe to form a conjugated probe. However, the free binding site of the enzyme reaction product may subsequently bind to a receptive material immobilized within the first detection zone 131 to form a new ternary sandwich complex. Alternatively, the enzyme reaction product may be detected using direct or indirect "competitive" assay formats. In such instances, the specific binding member of the probe may be the same as or an analog of the enzyme reaction product. Thus, upon reaching the detection zone 131, the detection probes and the enzyme reaction product compete for available binding sites of the immobilized receptive material. Of course, any other assay format is also suitable for use.

For the embodiment shown in FIG. 2, as enzyme concentration begins to increase in the test sample, more enzyme product reaction forms in the mixture. Thus, if a sandwich assay format is used, more enzyme reaction product binds to the detectable probes form conjugated probes so that the amount of enzyme is directly proportional to the signal intensity at the detection zone 131. On the other hand, if a competitive assay format is used, the amount of enzyme is indirectly proportional to the signal intensity at the detection zone 131. If desired, the signal intensity may be plotted versus the enzyme concentration for a range of known enzyme concentrations to generate an intensity curve. To determine the quantity of enzyme in an unknown test sample, the signal intensity may then be converted to enzyme concentration according to the intensity curve.

Figure 3:
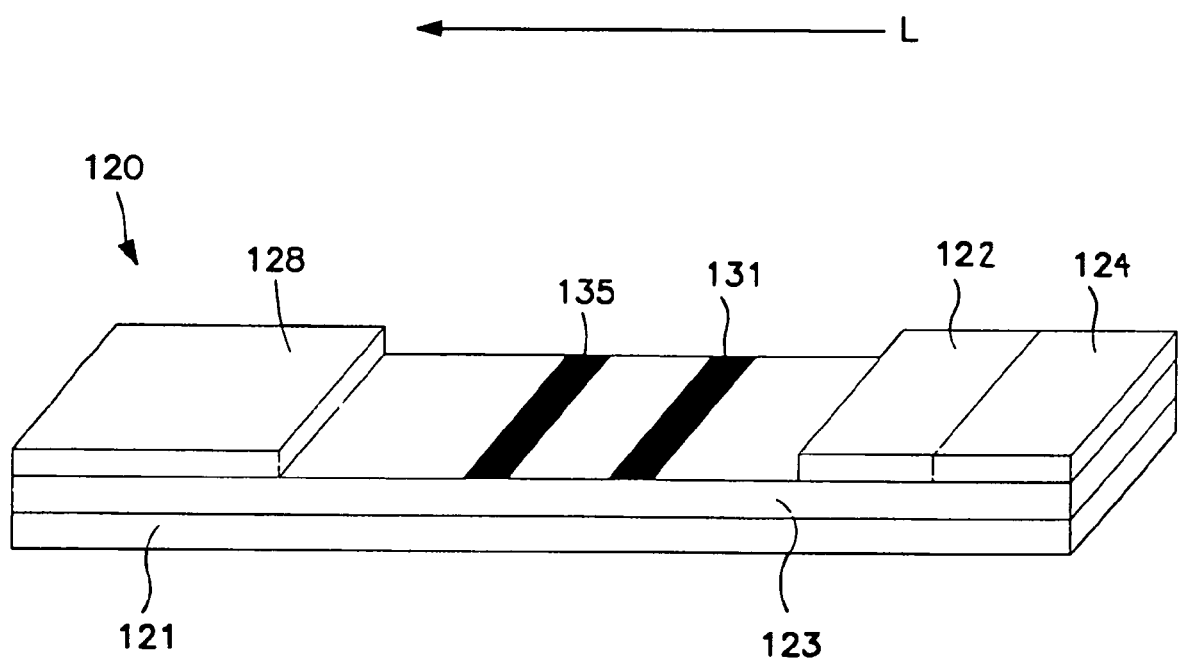
FIG. 3 is a perspective view of another embodiment of an assay device that may be used in a lateral flow assay device.

An assay device as disclosed herein may include additional zones on the device. For example, referring to FIG. 3, an assay device 120 is illustrated that is the same as the assay device 120 of FIG. 2, except that it also contains a second detection zone 135 positioned downstream from the detection zone 131. The second detection zone 135 may provide one or more distinct regions (e.g., line, dot, etc.), and may be positioned at any orientation relative to the flow of the mixture. A second receptive material is immobilized on the medium 123 within the second detection zone 135. The second receptive material may serve as a stationary binding site for any detectable substance that does not become bound within the first detection zone 131. In one embodiment, for example, in which a "direct" competitive assay is employed, the first receptive material contains an antibody that has a specific binding affinity for both the enzyme reaction product and the probes (i.e., the probes have a specific binding member bound thereto that is the same as or an analog of the enzyme reaction product). The second receptive material contains a polyelectrolyte that has a specific binding affinity for the probes. When present, the enzyme reaction product of the mixture competes with the probes for available binding sites of the first receptive material. Any remaining, unbound probes travel past the first detection zone 131 to the second detection zone 135. Because the probes have a specific affinity for the second receptive material, they become immobilized within the second detection zone 135.

Likewise, in another embodiment in which an "indirect" competitive assay is employed, the enzyme reaction product may contain a specific binding member (e.g., biotin) and the probes may be dyed particles bound with a complementary binding member (e.g., streptavidin) that has affinity for the enzyme reaction product. The first receptive material contains a specific binding member that is the same as or an analog of the enzyme reaction product, thereby having an affinity for the probes. The second receptive material contains a polyelectrolyte also having binding affinity for the probes. When present, the enzyme reaction product binds to the probes to form conjugated probes, thereby reducing the amount of probes otherwise available for binding to the first receptive material. Instead, those conjugated probes which are complexed to the enzyme reaction product, travel past the first detection zone 131 to the second detection zone 135. Because the probes have a specific affinity for the selected polyelectrolyte, they become immobilized within the second detection zone 135.

In the competitive assay embodiments referred to above, as the concentration of the enzyme increases, the signal intensity at the second detection zone 135, $I_2$, also begins to increase due to the presence of enzyme reaction product in the mixture. From this increase in signal intensity, the presence or concentration of the enzyme may be readily determined. For example, in one embodiment, the amount of enzyme is directly proportional to the signal intensity at the second detection zone 135, $I_2$. If desired, the signal intensity $I_2$ may be plotted versus the enzyme concentration for a range of known enzyme concentrations to generate an intensity curve. To determine the quantity of enzyme in an unknown test sample, the signal intensity may then be converted to enzyme concentration according to the intensity curve. It should be understood that, as discussed above with respect to the first detection zone 31 and/or 131, so long as one distinct region of the second detection zone 135 satisfies the direct relationship, the signal intensity exhibited by the second detection zone 135 is considered directly proportional to the enzyme concentration.

Also, in the embodiments referenced above, an inverse relationship may exist between the signal intensity at the detection zone 131 ($I_1$) and the second detection zone 135 ($I_2$). For example, because a predetermined amount of probes are present, the amount captured at the second detection zone 135 is inversely proportional to the amount captured at the detection zone 131. As a result of this inverse relationship, the concentration of the enzyme may, in some cases, be more effectively measured over an extended range by comparing the signal intensity at both detection zones. For example, in one embodiment, the amount of enzyme is directly proportional to the ratio of the signal intensity "$I_2$" to the signal intensity "$I_1$." Based upon the range in which this ratio falls, the general concentration range for the enzyme may be determined. If desired, the ratio of $I_2$ to $I_1$ may be plotted versus enzyme concentration for a range of known enzyme concentrations to generate an intensity curve. To determine the quantity of enzyme in an unknown test sample, the signal intensity ratio may then be converted to enzyme concentration according to the intensity curve. It should be noted that alternative mathematical relationships between $I_1$ and $I_2$ may be plotted versus the enzyme concentration to generate the intensity curve. For example, in one embodiment, the value of $I_2/(I_2+I_1)$ may be plotted versus enzyme concentration to generate the intensity curve.

A device may include additional detections zones. For instance, a device may include a detection zone within which a second component of a mixture may be detected. A receptive material may be immobilized within this second detection zone that is a specific binding member for the second component of the mixture. For instance, an enzyme reaction product may be bound and detected in a first detection zone, and a molecular substrate may be bound and detected in a second detection zone. Other zones that may be included on a device may include, for example, control zones, for ensuring that the device is working properly, one or more calibration zones, for providing internal calibration capability to the device, and the like.

As stated above, signal intensity may be determined qualitatively, quantitatively, and/or semi-quantitatively. In embodiments in which a quantitative result is desired, signal intensity may be determined using any of a variety of techniques known in the art. For example, in some embodiments, fluorescence detection techniques are utilized.

The aforementioned detection techniques are described specifically in the context of enzymes. However, as stated, the presently disclosed devices are equally suitable for detecting the presence or quantity of an enzyme inhibitor within a test sample. To detect the presence of an enzyme inhibitor within a test sample, a predetermined quantity of a corresponding enzyme may be mixed with the test sample and allowed to incubate. In the presence of a certain amount of an enzyme inhibitor, the enzyme-catalyzed reaction does not proceed at a detectable rate. Thus, the relationship between enzyme inhibitor concentration and signal intensity will be opposite to the relationship between enzyme concentration and signal intensity. For example, using FIG. 1 as an illustration, an enzyme-catalyzed reaction will not occur in the presence of a certain amount of inhibitor. Thus, no enzyme reaction product will form and the detection zone 31 will fail to generate a detectable signal. On the other hand, as the amount of enzyme inhibitor is reduced, the enzyme causes the enzyme reaction to form as described above. The signal intensity generated at the detection zone 31 thus begins to increase due to a corresponding increase in the presence of enzyme reaction product. Accordingly, in this particular embodiment, the amount of enzyme inhibitor within the test sample is inversely proportional to the signal intensity at the detection zone 31.

Figure 4:
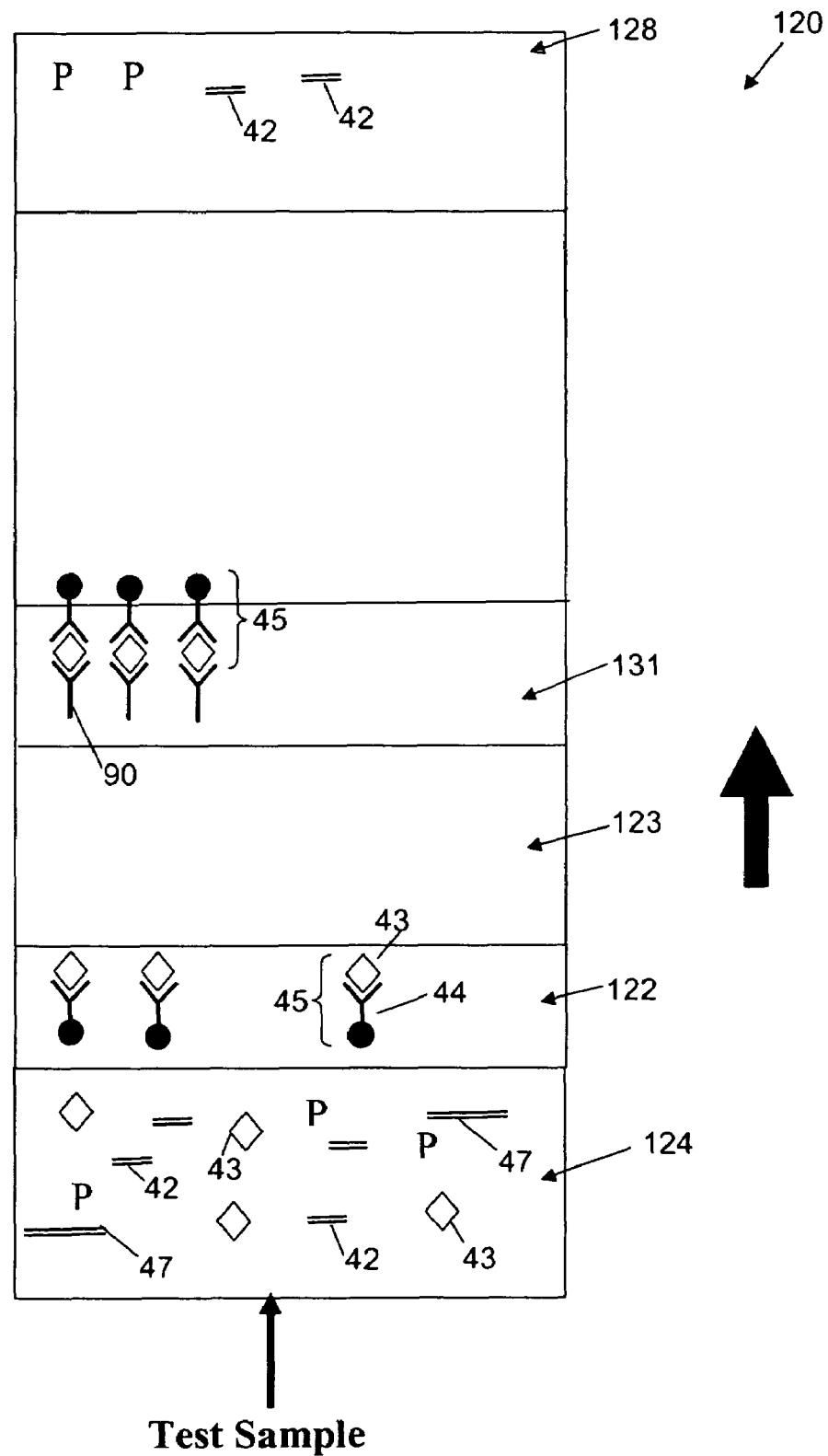
FIG. 4 is a schematic illustration of one assaying technique that may be used in one embodiment.

Referring to FIG. 4, one embodiment of a method for detecting the presence of a protease using fluorescence will now be described in more detail. Initially, a test sample containing a protease P is applied to sample application pad 124 where it contacts molecular substrates 47 (e.g., protein or glycoprotein). The molecular substrates 47 are allowed to contact the protease P and form a mixture that includes polypeptides 42 and 43 that are the enzyme reaction products of the enzyme-catalyzed reaction between the molecular substrates 47 and the protease P. The mixture also includes unreacted molecular substrates 47, and protease P. The mixture flows to the conjugate pad 122, as indicated by the directional arrow.

Diffusibly immobilized to the conjugate pad 122 are probes 44 that include a detectable substance and a specific binding member for enzyme reaction product 43. Upon interaction of the mixture with the probes 44 at the conjugate pad 122, enzyme reaction product 43 specifically bind to probes 44 to form conjugated probes 45. As probes 44 are diffusibly immobilized to conjugate pad 122, the mixture including the conjugated probes 45 then travels to the detection zone 131.

Immobilized within detection zone 131 is a receptive material 90 that is specific for a second binding site of the enzyme reaction products 43 generated by the enzyme-catalyzed reaction. Thus, the available binding sites in the detection zone 131 may be bound by the conjugated probes 45.

Once captured, the signal intensity of the conjugated probes 45 may be measured at detection zone 131. Fluorescence detection generally utilizes wavelength filtering to isolate the emission photons from the excitation photons, and a detector that registers emission photons and produces a recordable output, usually as an electrical signal or a photographic image. One suitable fluorescence detector for use is a FluoroLog III Spectrofluorometer, which is sold by SPEX Industries, Inc. of Edison, N.J. Another example of a suitable fluorescence detector is described in U.S. Patent Application Publication No. 2004/0043502 to Song, et al., which is incorporated herein in its entirety by reference thereto for all purposes. Although the use of fluorescence is utilized in this particular embodiment, it should be understood that any other known detection technique may also be utilized. For example, other suitable optical detection techniques may include, but are not limited to, phosphorescence, diffraction, reflectance, transmittance, etc. The optical reader may be capable of emitting light and also registering a detection signal (e.g., transmitted or reflected light, emitted fluorescence or phosphorescence, etc.). For example, in one embodiment, a reflectance spectrophotometer or reader may be utilized to detect the presence of reporters that exhibit a visual color (e.g. dyed latex microparticles). One suitable reflectance reader is described, for instance, in U.S. Patent App. Pub. No. 2003/0119202 to Kaylor, et al., which is incorporated herein in its entirety by reference thereto for all purposes.

Regardless of the technique used to measure signal intensity, the presence or the amount of the protease P may be ascertained by the signal intensity at the detection zone 131.

Figure 5:
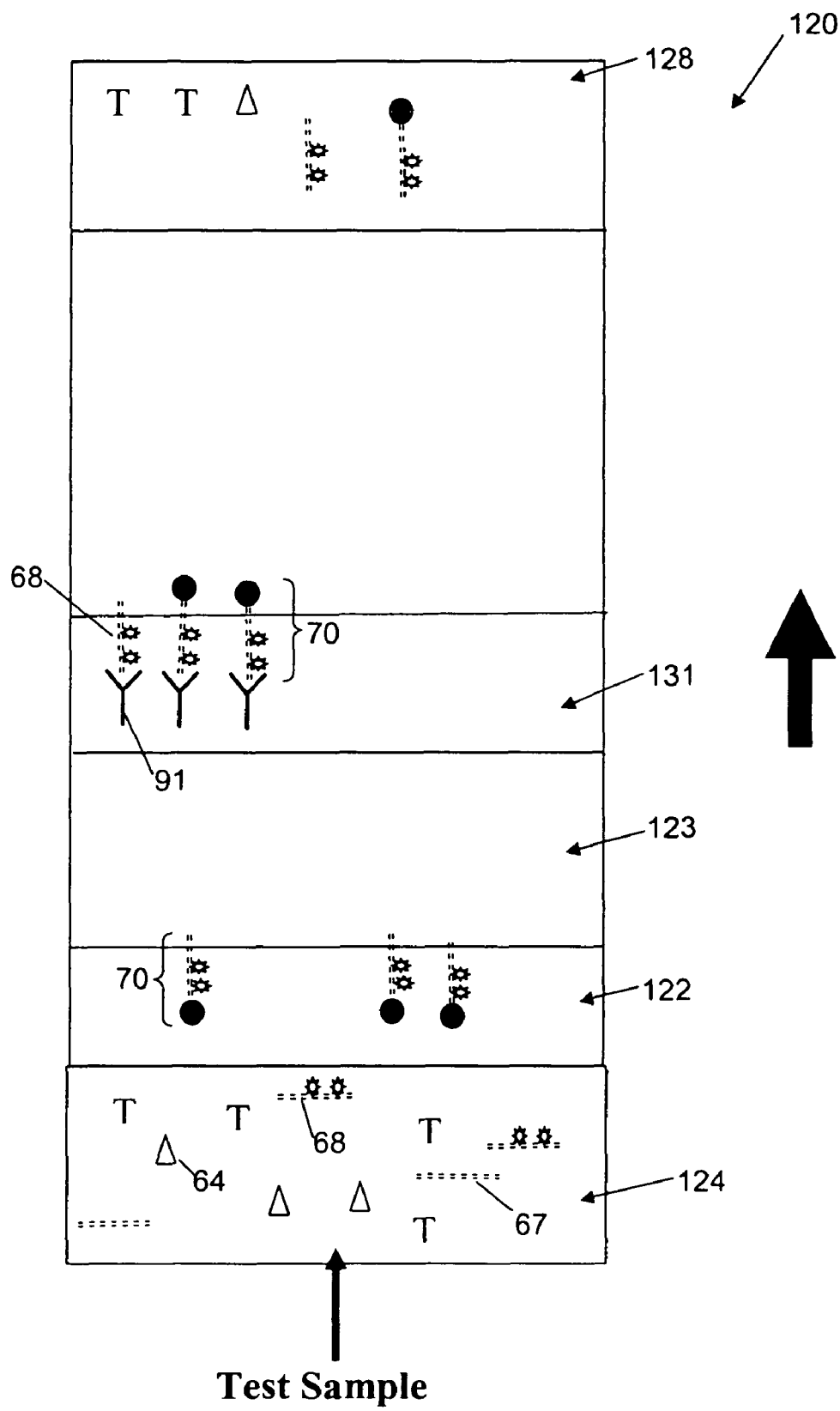
FIG. 5 is a schematic of another assaying technique that may be used in one embodiment.

Referring to FIG. 5, one embodiment of a method for detecting the presence of a transferase using fluorescence via a competitive type assay will now be described in more detail. Initially, a test sample containing a transferase T is applied to a sample application pad 124 that contains molecular substrates 67 (e.g., a polypeptide). The molecular substrates 67 are allowed to contact the transferase T for a sufficient period of time to form a mixture that includes components 64 (e.g., ATP) that may provide the moiety (e.g., phosphorous) targeted by the transferase. Following a contact period, which may simply be the period of time for flow from the sample application pad 124 to the conjugate pad 122, the mixture may include unreacted molecular substrates 67, transferase T, and product 68 generated by the enzyme-catalyzed reaction (e.g., a phosphorylated polypeptide). The mixture flows to the conjugate pad 122, as indicated by the directional arrow. Diffusibly immobilized on or in the conjugate pad 122 are detectable probes 70 that include the product of the enzyme catalyzed reaction or an analog thereof. As the mixture travels from the sample application pad 124 to the detection zone 131 the detectable probes 70 are picked up and travel with the mixture. Immobilized within detection zone 131 is a receptive material 91 that is specific for the product 68 generated by the enzyme-catalyzed reaction. Thus, the product 68 formed in the mixture and the detectable probes 70 compete for the available binding sites in the detection zone 131. Once captured, signal intensity may be measured and analyzed as described for other embodiments described herein. Specifically, in this embodiment a larger signal will indicate a lower concentration of transferase T in the test sample, as more of the available binding sites in the detection zone 31 will be occupied with the detectable probes 70.

Figure 6:
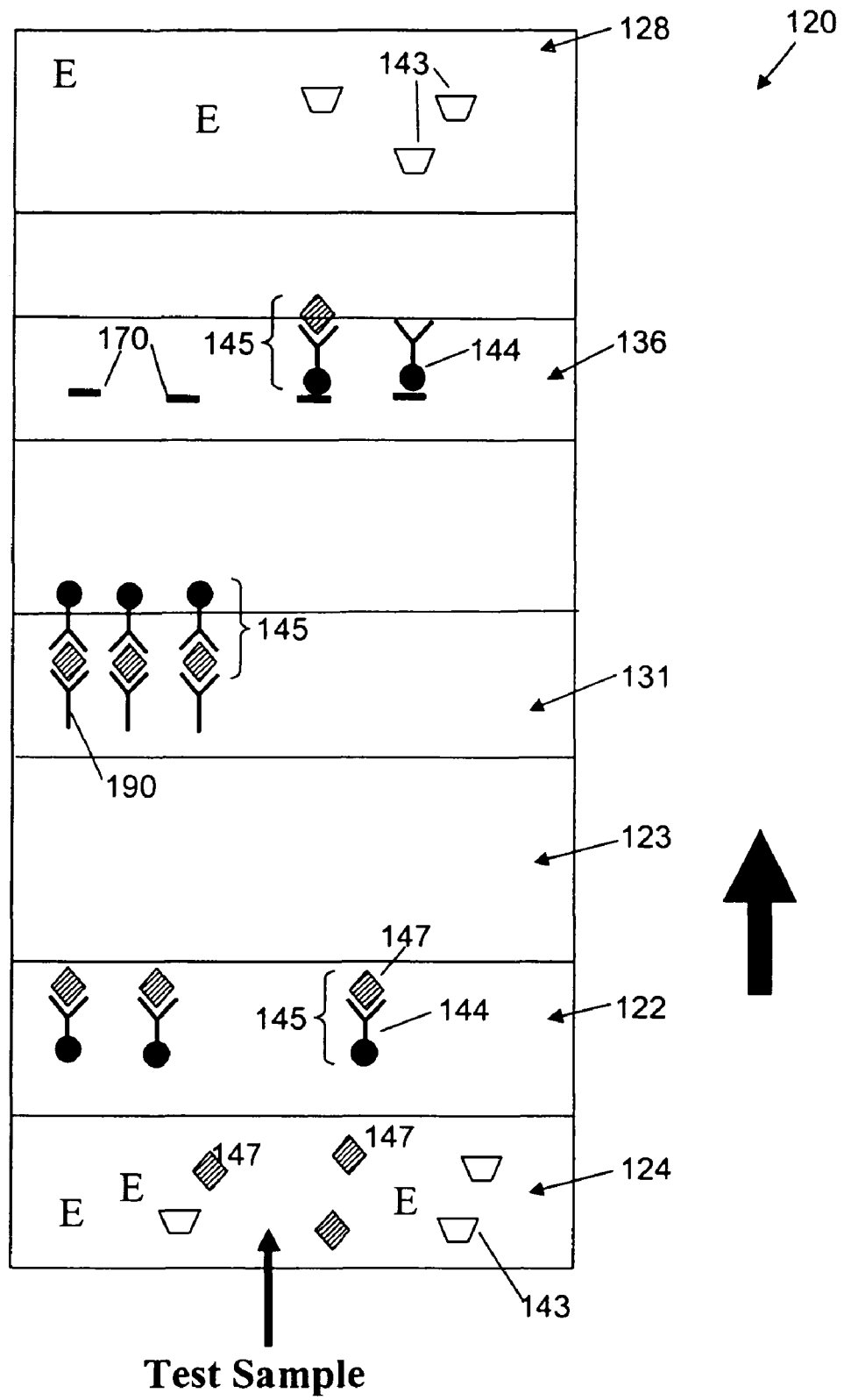
FIG. 6 is a schematic of another assaying technique that may be used in one embodiment.

FIG. 6 illustrates another embodiment of a test device including a control zone 136. According to this embodiment, a test sample including an enzyme E may be applied to the device at the sample application pad 124. The sample application pad 124 includes reagents for the enzyme catalyzed reaction including molecular substrates 147. The test sample combines with the reagents of the sample application pad 124 to form a mixture within which the enzyme-catalyzed reaction may take place to form at least one enzyme reaction product 143. The test sample may be held at the sample application pad 124 for a period of time as discussed above or may travel directly to a conjugate pad 122. Diffusibly immobilized at conjugate pad 122 are probes 144 including a detectable substance and a specific binding member for molecular substrates 147. Upon interaction of the test sample with the probes 144 at the conjugate pad 122, unreacted molecular substrates 147 remaining in the mixture specifically bind to probes 144 to form substrate conjugates 145. As probes 144 are diffusibly immobilized to conjugate pad 122, the mixture including any substrate conjugates 145 then travels to the detection zone 131. Immobilized within detection zone 131 is a receptive material 190 that is specific for a second binding site of the molecular substrates 147. Thus, the available binding sites in the detection zone 131 may be bound by the substrate conjugates 145. Once captured, the signal intensity of the substrate conjugates 145 may be measured at detection zone 131. For instance, a large signal intensity may indicate a high concentration of unreacted molecular substrates 147 in the mixture and accordingly, the presence of little or no enzyme in the test sample. The embodiment of FIG. 6 also includes a control zone 136 that gives a signal to the user that the assay is performing properly. For instance, the control zone 136 contains an immobilized polyelectrolyte receptive material 170 within the control zone 136 for capturing probes that can include both substrate conjugate probes 145 and probes 144.

In one exemplary application, the assay device may be used for determining the presence of transferase enzymes involved in the RAS protein activation cycle. RAS proteins function as important molecular switches for a wide variety of signal pathways. These pathways control processes including cytoskeleton integrity, cell adhesion and migration, and apoptosis. RAS proteins cycle between an activated form (RAS-GTP) and an inactivated form (RAS-GDP).

RAS proteins are often deregulated in cancers, leading to increased invasion and metastasis as well as decreased apoptosis. Accordingly, the assay device may be utilized for determination of the presence of GTPase-activating proteins (GAPs) that increase the rate of GTP hydrolysis, returning RAS-GTP to its inactive RAS-GDP form. For instance, a test sample containing a GAP may be mixed with RAS-GTP molecular substrate. The molecular substrate is allowed to contact the test sample for a sufficient period of time to form a mixture that may include unreacted molecular substrate (RAS-GTP), GAP, and product generated by the enzyme-catalyzed reaction (RAS-GDP). The mixture is allowed to flow to the conjugate pad that contains detectable probes labeled with a specific binder for either the molecular substrate (RAS-GTP) or the product of the enzyme-catalyzed reaction (RAS-GDP). For instance, the probes may be labeled with a MAP kinase that is activated by RAS-GTP in certain metabolic pathways. Upon combination, unreacted molecular substrate may specifically bind to the MAP kinase-labeled probed to form substrate conjugates, as described above, and the mixture then travels to a detection zone. Immobilized within the detection zone is a second receptive material that is specific for the RAS-GTP, for instance a second MAP kinase. Thus, the available binding sites in the detection zone may be occupied by the substrate conjugates formed in the conjugate pad that include the unreacted substrate. The fluorescent particles joined to the detectable probes therefore will also be bound in the detection zone. Once captured, signal intensity may be measured and analyzed as described for other embodiments described herein to determine the presence of GAPs in the test sample.

In another embodiment, a lateral flow assay device may be utilized to determine the presence of RAS activating proteins. For instance, the lateral flow assay device may be utilized to determine the presence of G exchange factors (GEF) (e.g., CDC25, SOS1, SOS2) that catalyze the reactivation of RAS-GDP to its active form, RAS-GTP. According to this embodiment, the molecular substrates may be the inactive form of the protein, RAS-GDP. Upon contact of the molecular substrates with the test sample containing the activating GEF, the RAS-GDP may be activated to the RAS-GTP form. In this case, the product (RAS-GTP) may be conjugated to a detectable substance at a conjugate pad and then captured by a specific binder, e.g., a MAP kinase, immobilized in the detection zone to determine the presence or quantity of GEF in the test sample.

Another exemplary application of the lateral flow assay device may be in the determination of the presence of angiotensin-converter enzyme (ACE) in a test sample. ACE is an exopeptidase that catalyzes the conversion of angiotensin I to angiotensin II. While angiotensin I appears to exist primarily as a precursor to angiotensin II, angiotensin II is a potent vasoconstrictor and believed to play a role in conditions such as high blood pressure, heart disease and diabetic nephropathy. According to this particular embodiment, the lateral flow assay device may include a molecular substrate such as angiotensin I. Upon contact of the molecular substrate with the test sample containing ACE, the angiotensin I may be converted to angiotensin II. The detection zone of the lateral flow assay device may contain immobilized therein a receptive material that is specific for angiotensin II, such as $AT_1$ or $AT_2$ receptors, for example. The binding and detection of the detectable probes (e.g., angiotensin II conjugated probes formed at a conjugate pad) in the detection zone may indicate the presence of ACE in the test sample.

Lateral flow assay devices as described herein may provide a relatively simple and cost-efficient method to quickly perform on-site testing of enzymes or their inhibitors. The device may provide a test result that is visible so that it is easily observed by the person performing the test in a prompt manner and under test conditions conducive to highly reliable and consistent test results. The lateral flow assay device is also disposable so that, if desired, it may be discarded when the test is concluded.

The present disclosure may be better understood with reference to the following examples.

EXAMPLE 1

To prepare a substrate, hemoglobin was biotinylated in borate buffer using EX-LC-biotin available from Pierce Biotechnology. The biotinylated hemoglobin was purified via dialysis.

A lateral flow device was prepared as follows:

To form the sample pad, a glass fiber pad was soaked with the purified biotinylated hemoglobin dissolved in PBS buffer containing sucrose/Tween-20. The glass fiber pad was then dried at 37° C.

To form the conjugate pad, a second glass fiber pad was soaked with a solution including blue particles tagged with streptavidin available from Bangs Laboratories, Inc., sucrose, and Tween-20. The second glass fiber pad was then dried.

A nitrocellulose membrane card was striped with anti-biotin antibody to form a detection zone and also striped with polylysine to form a control zone. The nitrocellulose membrane card was dried following application of the materials.

The conjugate pad and a cellulose pad were then laminated at either end of the nictrocellulose membrane card with the detection zone and the control zone therebetween. A reagent-free glass fiber pad and the hemoglobin-loaded glass fiber sample pad were also laminated to the nitrocellulose membrane card. Specifically, the reagent-free glass fiber pad was laminated between the conjugate pad and the hemoglobin-loaded sample pad to modulate the enzyme reaction time. The assembled card was then cut into several devices, each approximately 4 mm in width.

Assays were conducted with the formed devices. Protease from S. Griseus was diluted in PBS buffer in various concentrations and directly applied to the hemoglobin-loaded sample pad. The mixture thus formed flowed from the sample pad to the reagent-free glass fiber pad and on to the conjugation pad, the detection zone, and the control zone, respectively.

Figure 7:
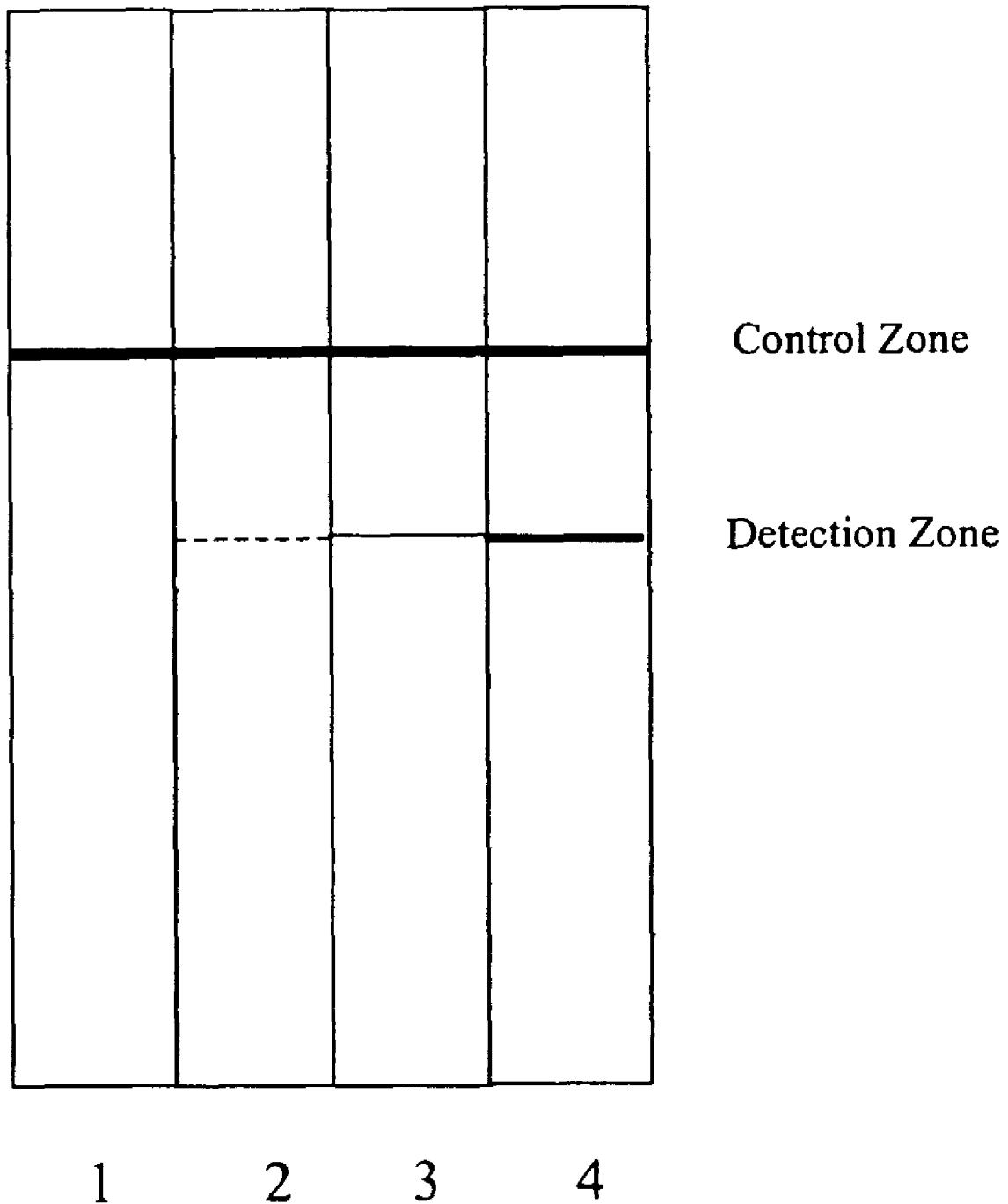
FIG. 7 schematically illustrates results obtained for one embodiment of an assay device as described herein.

Results for a typical run are schematically illustrated in FIG. 7. Lanes 1-4 of the illustrated assay device were treated with protease at a concentration of 30 µg/mL, 0.3 µg/mL, 0.03 µg/mL, and a control of 0.0 µg/mL, respectively. Approximately twenty minutes following application, two strong blue bands were observed at the detection zone in lanes 3 and 4, to which samples including little or no protease were applied. In contrast, a weak band or no band at all was observed at the detection zone in lanes 1 and 2—those samples including a high concentration of the protease. All lanes showed a strong blue band in the control zone.

While the subject matter has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present disclosure should be assessed as that of the appended claims and any equivalents thereto.

What is claimed is:

1. A lateral flow assay device for detecting the presence or quantity of an enzyme, or an inhibitor thereof, within a test sample, the lateral flow assay device comprising a chromatographic medium defining a first detection zone and a second detection zone, the chromatographic medium further defining an application area within which a molecular substrate is diffusibly immobilized, wherein said test sample contacts said molecular substrate within said application area, the molecular substrate being capable of undergoing a reaction catalyzed by the enzyme to form a product, the lateral flow assay device further defining a conjugate zone downstream of said application area, a first detectable substance being diffusibly immobilized within said conjugate zone, said first detectable substance directly or indirectly binding with said product to generate a first detection signal, the lateral flow assay comprising a second detectable substance that directly or indirectly binds with said molecular substrate to generate a second detection signal, wherein the presence or quantity of an enzyme, or an inhibitor thereof, is determinable from said first detection signal within said first detection zone and said second detection signal within said second detection zone.

2. The lateral flow assay device of claim 1, wherein said molecular substrate comprises a first specific binding member and wherein said product comprises a second specific binding member.

3. The lateral flow assay device of claim 2, wherein said first detectable substance is directly or indirectly bound to a third specific binding member.

4. The lateral flow assay device of claim 3, wherein said third specific binding member has affinity for said second specific binding member.

5. The lateral flow assay device of claim 1, wherein a first receptive material is immobilized within said first detection zone, said first receptive material binding said product.

6. The lateral flow assay device of claim 1, wherein a second receptive material is immobilized within said second detection zone, said second receptive material binding said molecular substrate.

7. The lateral flow assay device of claim 6, wherein the amount of an enzyme within the test sample is directly proportional to the intensity of said second detection signal.

8. The lateral flow assay device of claim 1, wherein the lateral flow assay device detects the presence or quantity of a hydrolase.

9. The lateral flow assay device of claim 8, wherein the hydrolase is a protease or peptidase.

10. The lateral flow assay device of claim 9, wherein said molecular substrate is casein, albumin, hemoglobin, myoglobin, keratin, gelatin, insulin, proteoglycan, fibronectin, laminin, collagen, elastin, or a derivative thereof.

11. A lateral flow assay device for detecting the presence or quantity of an enzyme, or an inhibitor thereof, within a test sample, the lateral flow assay device comprising a chromatographic medium defining a first detection zone and a second detection zone, the chromatographic medium further defining an application area within which a molecular substrate is diffusibly immobilized, wherein said test sample contacts said molecular substrate within said application area, the molecular substrate being capable of undergoing a reaction catalyzed by said enzyme to form a product, the molecular substrate comprising a first specific binding member and the product comprising a second specific binding member, the lateral flow assay device further comprising a first detectable substance diffusibly immobilized in a conjugate zone that is downstream of said application area, the first detectable substance being capable of generating a first detection signal, the lateral flow assay device comprising a second detectable substance capable of generating a second detection signal, said first detectable substance being directly or indirectly bound to a third specific binding member that is the same as or an analog of said first specific binding member and said second detectable substance being directly or indirectly bound to a fourth specific binding member that is the same as or an analog of said second specific binding member, wherein the presence or quantity of an enzyme, or an inhibitor thereof, is determinable from said first detection signal within said first detection zone and said second detection signal with in said second detection zone.

12. The lateral flow assay device of claim 11, wherein a first receptive material is immobilized within said first detection zone, said first receptive material binding said first specific binding member or an analog thereof.

13. The lateral flow assay device of claim 11, wherein a second receptive material is immobilized within said second detection zone, wherein said second receptive material is capable of directly or indirectly binding to said second specific binding member or an analog thereof.

14. The lateral flow assay device of claim 13, wherein the amount of an enzyme within the test sample is directly proportional to the intensity of said second detection signal.

15. The lateral flow assay device of claim 11, wherein the lateral flow assay device detects the presence or quantity of a hydrolase.

16. The lateral flow assay device of claim 15, wherein the hydrolase is a protease or peptidase.

17. The lateral flow assay device of claim 16, wherein said molecular substrate is casein, albumin, hemoglobin, myoglobin, keratin, gelatin, insulin, proteoglycan, fibronectin, laminin, collagen, elastin, or a derivative thereof.

18. The lateral flow assay device of claim 2, wherein said second detectable substance is directly or indirectly bound to a fourth specific binding member.

19. The lateral flow assay device of claim 18, wherein said fourth specific binding member has an affinity for said first specific binding member.

* * * * *